(12) United States Patent
Gramse et al.

(10) Patent No.: US 7,337,002 B2
(45) Date of Patent: Feb. 26, 2008

(54) IMPLANTABLE MEDICAL DEVICE WITH DETACHABLE BATTERY COMPARTMENT

(75) Inventors: Leonard J. Gramse, St. Paul, MN (US); Robert J. Hanowski, St. Paul, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 730 days.

(21) Appl. No.: 10/643,369

(22) Filed: Aug. 19, 2003

(65) Prior Publication Data
US 2005/0043769 A1    Feb. 24, 2005

(51) Int. Cl.
*A61N 1/375*    (2006.01)
(52) U.S. Cl. .............................. 607/36; 607/33; 607/34
(58) Field of Classification Search ................... 607/33, 607/34, 36
See application file for complete search history.

(56) References Cited

U.S. PATENT DOCUMENTS

| 4,010,760 | A | * | 3/1977 | Kraska et al. ................. 607/36 |
|---|---|---|---|---|
| 4,119,103 | A | | 10/1978 | Jirak |
| 5,314,451 | A | | 5/1994 | Mulier |
| 5,411,538 | A | | 5/1995 | Lin |
| 5,573,551 | A | | 11/1996 | Lin et al. |
| 6,269,266 | B1 | | 7/2001 | Leysieffer |
| 6,894,456 | B2 | | 5/2005 | Tsukamoto et al. |
| 7,009,362 | B2 | | 3/2006 | Tsukamoto et al. |

* cited by examiner

*Primary Examiner*—George R. Evanisko
*Assistant Examiner*—Michael Kahelin
(74) *Attorney, Agent, or Firm*—Schwegman, Lundberg & Woessner, P.A.

(57) ABSTRACT

An implantable medical electronic tissue stimulating device is formed of two hermetically sealed, fluid impervious housings, one containing an electronic pulse generator and the other a battery power supply. The two are adapted to be mechanically and electrically coupled together through a coupler/connector whereby current from the battery in one sealed housing is fed to the electronic pulse generator in the other sealed housing.

6 Claims, 5 Drawing Sheets

IMPLANTABLE MEDICAL DEVICE WITH DETACHABLE BATTERY COMPARTMENT

BACKGROUND OF THE INVENTION

I. Field of the Invention

This invention relates generally to implantable medical tissue stimulating devices, and more particularly to a hermetically sealed pulse generator with an independent, hermetically sealed battery compartment.

II. Discussion of the Prior Art

Implantable pacemakers, cardiac defibrillators and neural stimulators typically comprise a single hermetically sealed case or housing containing a microprocessor and a pulse generator controlled by the microprocessor for delivering tissue stimulating pulses at programmed time intervals along with a battery power supply for supplying electrical current to the electronic circuitry. Given the complexity and capabilities of present-day tissue stimulators, they may have a manufacturing cost approaching ranging between $1,000.00 and $3,000.00.

The battery power supply may typically comprise a lithium iodide cell in that such batteries do not generate a gas during discharge that would make the sealing of the implantable device problematic. Implantable medical devices of the type described herein have a somewhat limited shelf life and a substantial cost burden is incurred by the manufacturers of such devices in the event that sales do not deplete the inventory quickly enough. In that the battery and the somewhat expensive electronics are necessarily contained within a hermetically sealed container or housing, the entire device must be scrapped if the unit is not implanted within a period of 12 months of manufacture for certain modules and 24 months for others. Taking into account the number of different models of pacemakers and AICDs manufacturers produce and the need to maintain an inventory of each, losses due to scrapping can easily reach several million dollars per year due to battery depletion.

During the test and burn-in phase of manufacture, the implantable device is subjected to elevated temperatures to stress the integrated circuits and other components of the microprocessor-controlled pulse generator to detect hardware faults. The elevated temperatures are known to cause battery degradation.

Thus, a need exists for an implantable tissue stimulator that will have a fresh, fully charged battery at the time of implant irrespective of the date of manufacture. The present invention provides a solution.

SUMMARY OF THE INVENTION

The problems with the prior art design discussed above are resolved in accordance with the present invention by providing an implantable medical tissue stimulating device that comprises an electronic pulse generator contained in a first hermetically sealed housing member, a battery power supply contained in a second hermetically sealed housing member and a means for mechanically and electrically coupling the first and second housing members together at the time of implant whereby a fresh battery begins to furnish energy to the electronic circuitry at the time of implant rather than at the time of manufacture of the pulse generator.

DESCRIPTION OF THE DRAWINGS

The foregoing features, objects and advantages of the invention will become apparent to those skilled in the art from the following detailed description of a preferred embodiment, especially when considered in conjunction with the accompanying drawings in which like numerals in the several views refer to corresponding parts.

DESCRIPTION OF THE PREFERRED EMBODIMENT

Figure 1:
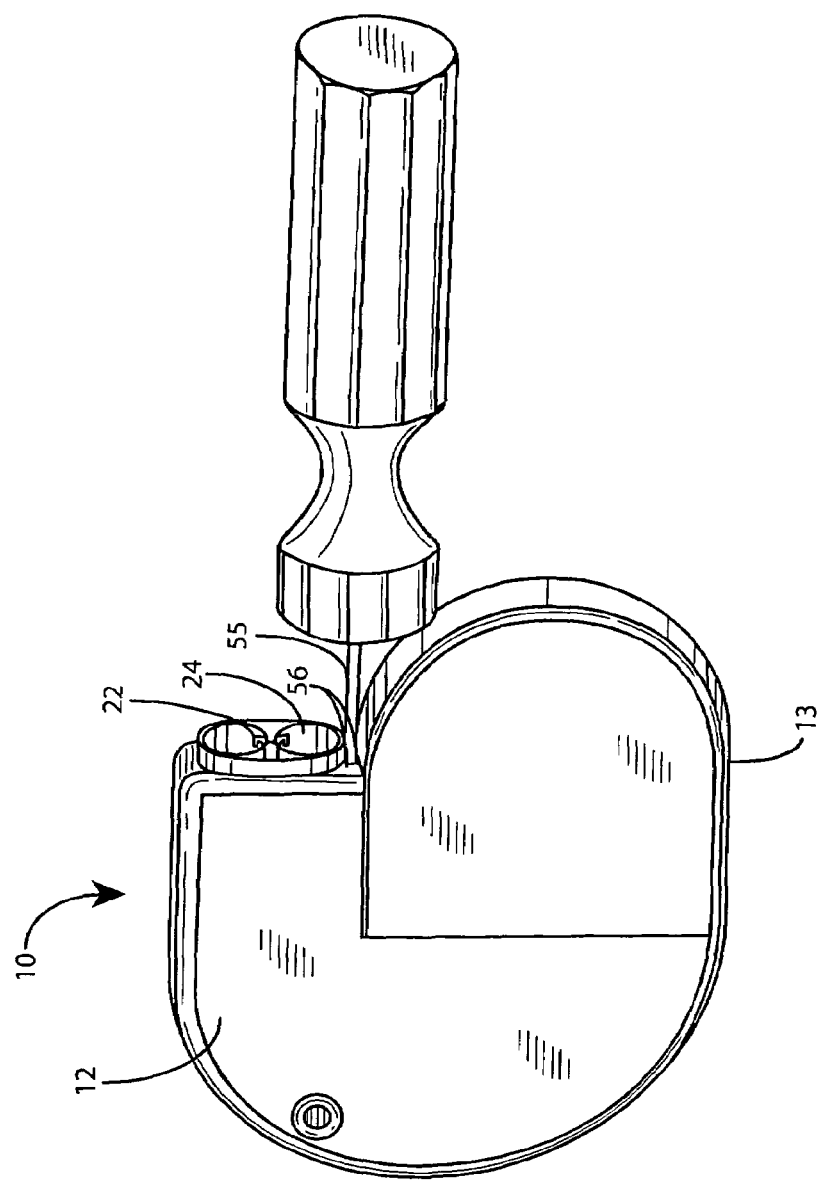
FIG. 1 is an isometric view of an implantable medical tissue stimulator constructed in accordance with the present invention where the battery compartment and the pulse generator compartment are joined to one another.

In FIG. 1 there is indicated generally by numeral 10 and implantable medical tissue stimulating device, such as an implantable pacemaker, an automatic implantable cardiac defibrillator or other type of tissue stimulator known in the art. It is seen to comprise a first hermetically sealed housing or compartment 12 that is designed to contain the electronic circuitry comprising a microprocessor-controlled pulse generator and a second hermetically sealed housing 13 for containing an electrochemical cell or battery for powering the electronic circuitry.

Figure 2:
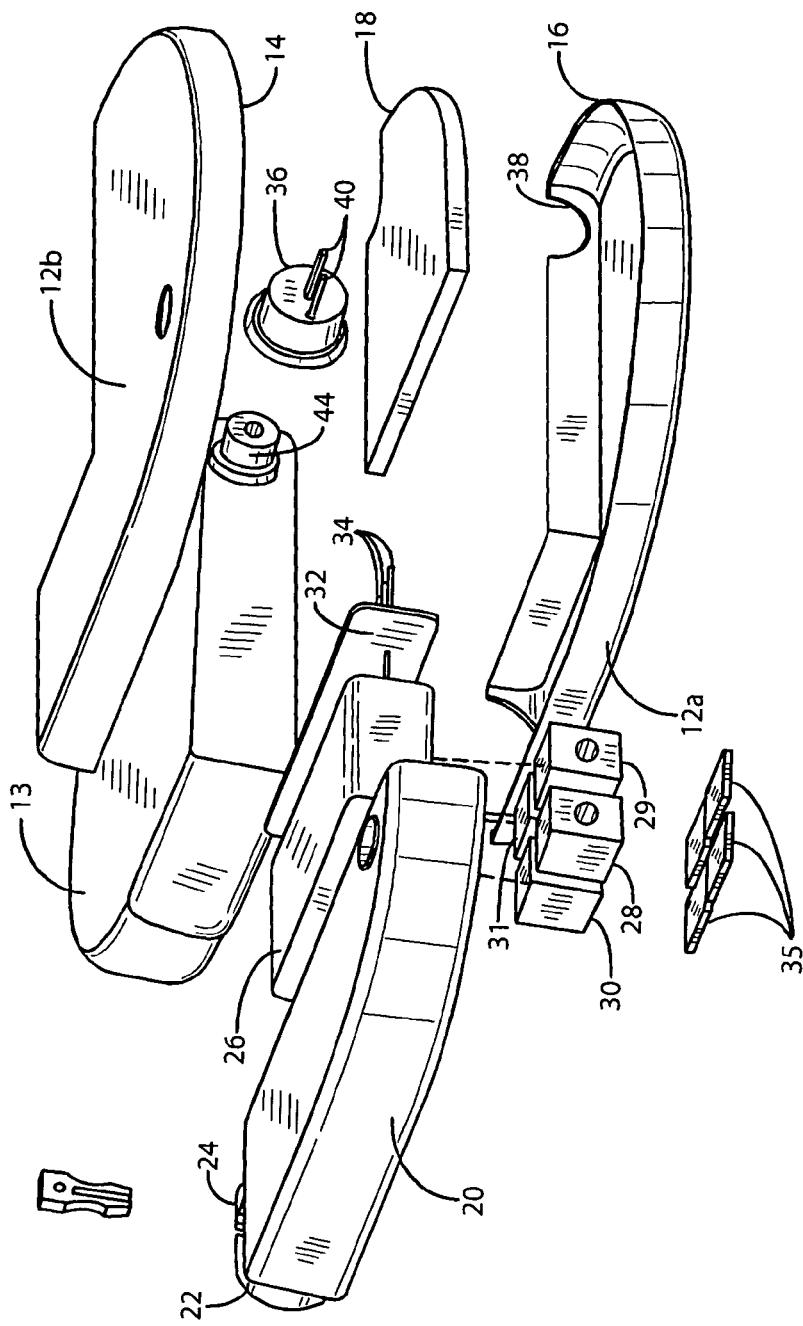
FIG. 2 is an exploded view illustrating the parts comprising the electronics compartment.

As is shown in the exploded view of FIG. 2, the housing 12 is preferably fabricated from a metal, such as titanium, and is comprised of two halves 12a and 12b that are brought together and joined by welding along their mating edges 14 and 16. Before welding the two halves together, an electronic circuit module 18 is placed in the housing, as is a lead connector block assembly that comprises a metal shell 20 having lead receiving bores as at 22 and 24 and a pocket into which is fitted a connector block 26. The connector block 26 is formed from an insulating material and includes longitudinally extending bores that are adapted to receive the proximal terminal connectors on medical leads (not shown) that plug into the openings 22 and 24 of the shell 20. Fitted into the connector block 26 is a plurality of conductive lead locking blocks 28, 29, 30 and 31 into which contact areas on the proximal terminal end of the medical lead are intended to mate. The connector block assembly includes a feedthrough member 32 that becomes welded to the base of the shell 20 to provide rf isolation. First, however, conductive pins 34 on the feedthrough member 32 are welded to the contact blocks 28-31 and to predetermined nodes on the electronic circuit module 18. Insulating pads, as at 35 fit between the contact blocks and electrically isolate the contact blocks and feedthrough pins from the shell 20.

Thus, when the housing halves 12a and 12b are brought together and welded, the electronic circuitry, as well as the connector for the proximal terminal of medical leads, are hermetically sealed within the housing. Also, a battery coupler/connector 36 is fitted into semicircular sockets 38 formed in the two housing halves 12a and 12b and welded in place. The positive and negative poles 40 of the coupler/connector 36 are welded to appropriate tie points on the electronic circuit 18 prior to placement of the surrounding housing 12.

Referring again to FIG. 1, the second hermetically sealed housing member 13 contains a battery power supply that when appropriately coupled to the housing member 12 provides the necessary energization for the electronic circuit module 18.

As best seen in FIG. 2, the battery housing 13 includes a male coupler/connector member 44 that is adapted to mate with the female coupler 36 forming part of the first housing 12 for the electronics circuitry.

Figure 3:
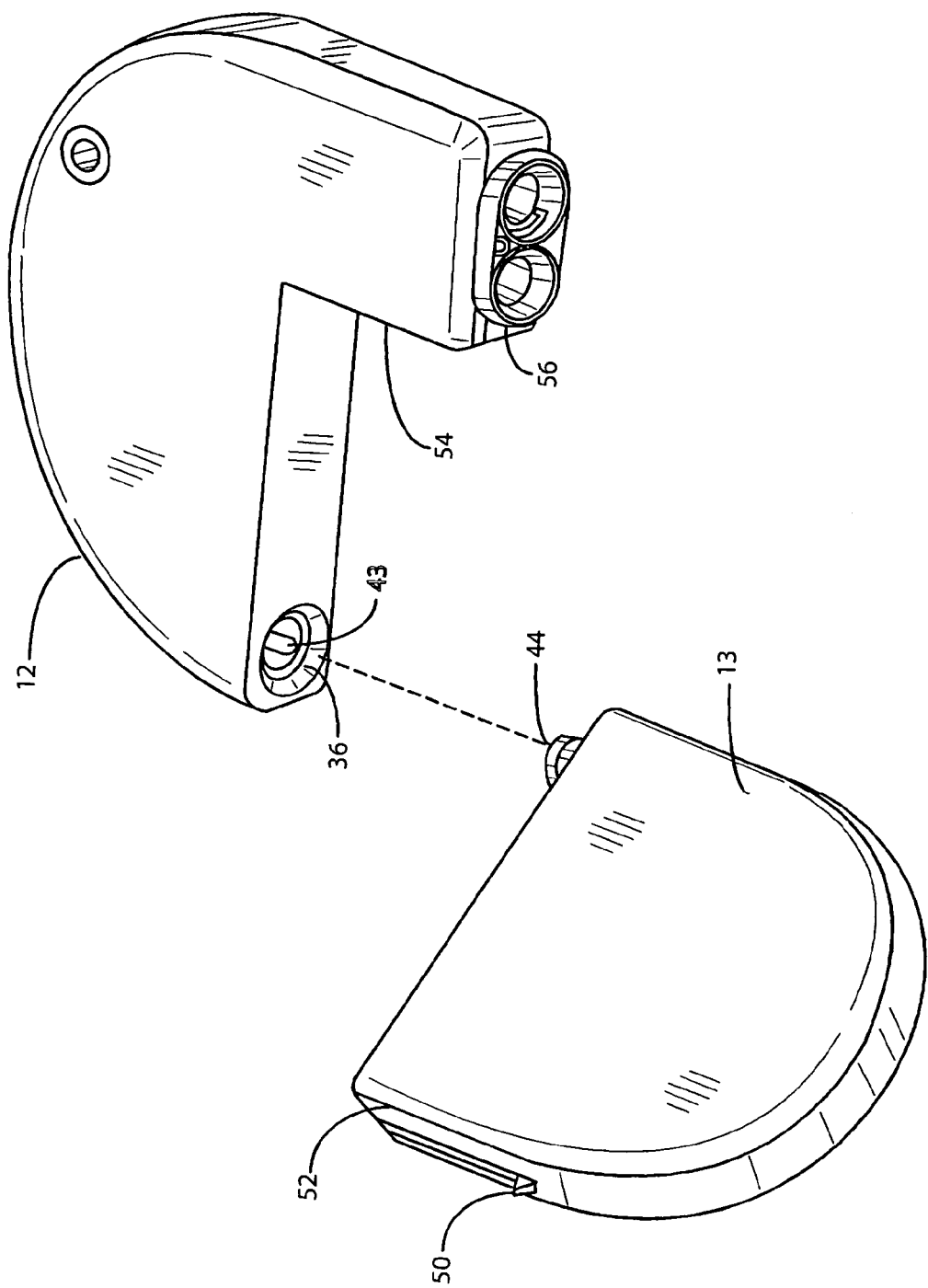
FIG. 3 is an exploded view showing the battery compartment disconnected from the pulse generator compartment.

Referring next to FIG. 3, when the battery coupler/connector member 44 is inserted into the coupling member 36 of the hermetically sealed electronic circuit housing member 12 and then the battery housing 13 is rotated approximately 90° so that the battery housing and the circuit housing become aligned as in FIG. 1, the two housing halves become positively locked together. This is achieved by providing a helical thread 46 of a predetermined pitch on the battery terminal 44 and that mates with an internal thread formed in the female coupler 36.

Figure 5:
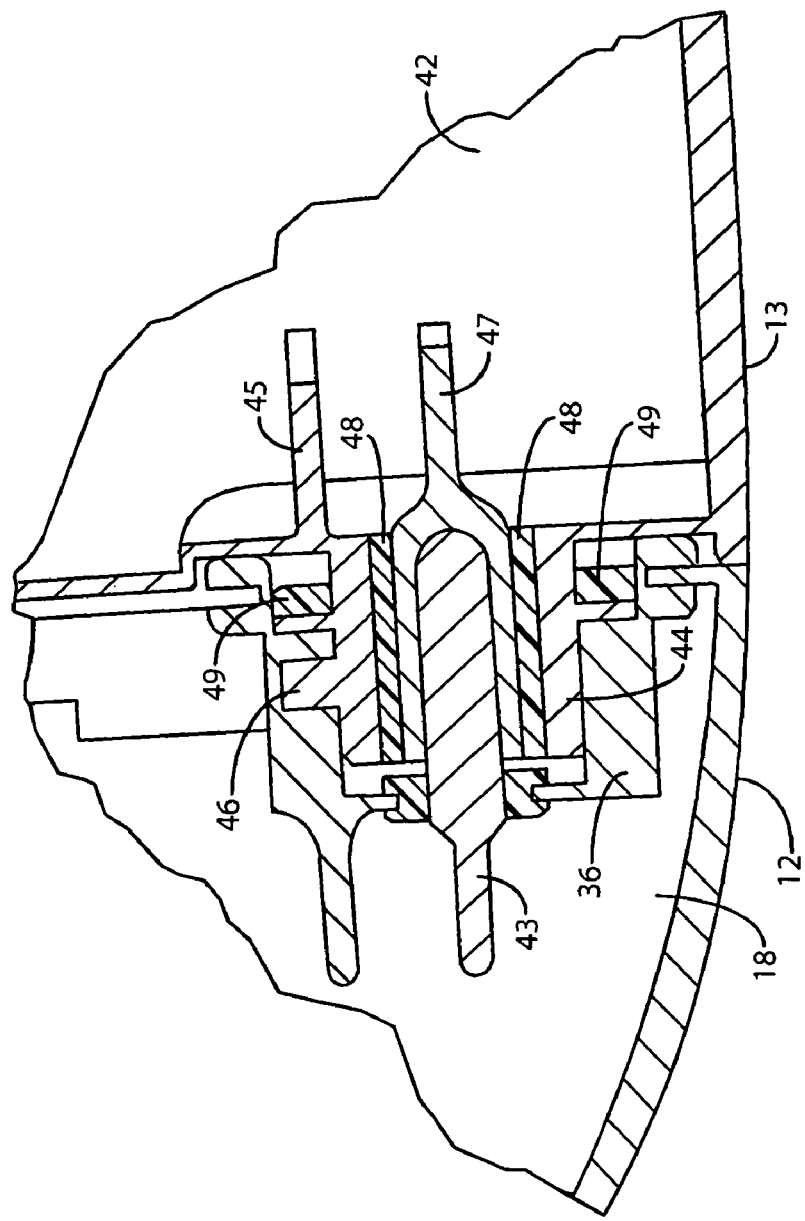
FIG. 5 is an enlarged cross-sectional view taken through the coupling/connector and seal mechanically and electrically joining the battery compartment to the pulse generator compartment.

Illustrated in FIG. 5 is a cross-sectional view taken through the battery housing 13 showing the chemical cell 42 and through the coupler/connector member 44 and the mating female coupler socket 36 to show their internal construction. The socket 36 forms one conductor for mating with a first battery terminal 45 while the center post 43 mates with the second battery terminal 47. An insulating tube 48 surrounds battery terminal 47 and electrically isolates it from the terminal 46.

Built into the above-described mechanism for removably coupling the first and second housing members to one another is an elastomeric seal 49 preventing ingress of body fluids into the interface between the male battery coupler/connector member 44 and the female coupler socket 36.

Figure 4:
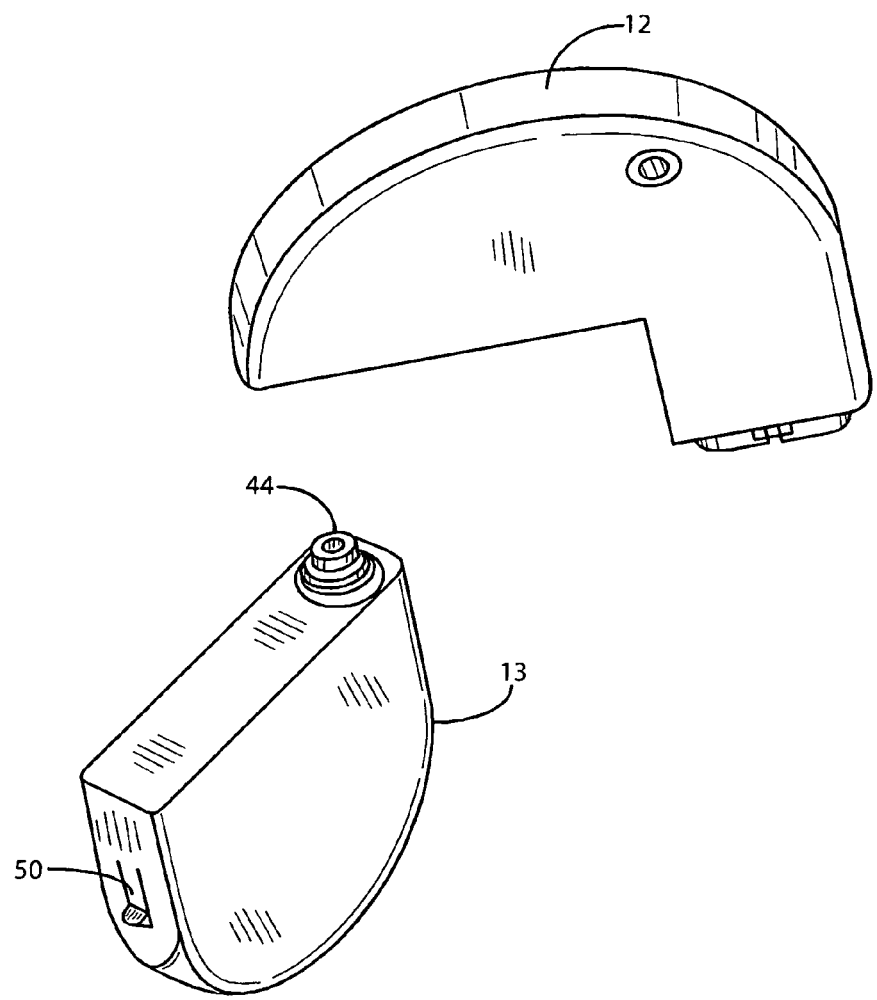
FIG. 4 is a perspective view similar to FIG. 2 but illustrating the male coupling/connector portion incorporated into the battery compartment.

To prevent rotation of the battery housing 13 relative to the circuit housing 12 once the coupler members 36 and 44 are joined, a spring biased latch 50 projects from a side surface 52 of the battery housing 13 as shown in FIGS. 3 and 4. The latch 50 is designed to fit into an associated groove (not shown) formed midway across the width dimension of the projecting portion 54 of the housing 12. If it becomes necessary to uncouple the battery from the electronics portion of the implantable device, a suitable needle probe 55 (FIG. 1) may be inserted into the groove at its entrance point 56 whereby the barb of latch 50 can be depressed so as to no longer reside in the groove, at which point the battery housing 13 can be rotated to uncouple the threaded connection between the two coupler/connector members 36 and 44.

Thus, it can be seen that a secure mechanical and electrical connection can be established between the battery supply 42 contained within the housing member 13 and the electronic circuitry contained within the housing member 12 such that the necessary operating voltages become available to the electronic circuitry. Since this connection can be made at the time of implant, it is assured that the battery will be fresh and need not have been subjected to the elevated temperatures used during the test and bum-in phase of manufacture of the device.

This invention has been described herein in considerable detail in order to comply with the patent statutes and to provide those skilled in the art with the information needed to apply the novel principles and to construct and use such specialized components as are required. However, it is to be understood that the invention can be carried out by specifically different equipment and devices, and that various modifications, both as to the equipment and operating procedures, can be accomplished without departing from the scope of the invention itself.

What is claimed is:

1. An implantable, medical-tissue-stimulating device comprising:
   (a) an electronic pulse generator contained in a first, hermetically-sealed, body-fluid-impervious, housing member, the first housing member including an internally-threaded, female socket formed of an electrically-conductive material, the female socket containing a concentrically-disposed, conductive, terminal pin;
   (b) a battery power supply contained in a second, hermetically-sealed, body-fluid-impervious, housing member, the second housing member including an externally-threaded, outwardly-projecting, tubular, electrically-conductive terminal member containing an insulating sleeve surrounding a concentrically-disposed, female contact; and
   (c) the internally-threaded, female, socket adapted to receive the externally-threaded terminal member therein, whereby rotation of the first housing member relative to the second housing member, through approximately ninety degrees, urges the first and second housing members together in a coplanar relationship with the terminal pin mating with the concentrically-disposed female contact.

2. The implantable medical tissue stimulating device as in claim 1 wherein the first and second housing members are formed from a metal.

3. The implantable medical tissue stimulating device as in claim 1 wherein the first and second housing members are formed from titanium.

4. The implantable medical tissue stimulating device as in claim 1 and further including a fluid-impervious seal disposed between the terminal member and the female socket.

5. The implantable medical tissue stimulating device as in claim 1 and further including a fluid impervious seal disposed between the female socket and the terminal pin for preventing body fluids from reaching the electronic pulse generator.

6. The implantable medical tissue stimulating device as in claim 1 and further including a latch member on one of the first and second housing members for engaging a groove on the other of the first and second housing members for retaining the first and second housing members in their coplanar relation.

* * * * *